United States Patent [19]

Nand et al.

[11] 4,148,611
[45] Apr. 10, 1979

[54] TEST COMPOSITION, DEVICE AND METHOD FOR THE DETECTION OF PEROXIDATIVELY ACTIVE SUBSTANCES

[75] Inventors: Shradha Nand, Elkhart; Melvin D. Smith, Wakarusa, both of Ind.

[73] Assignee: Miles Laboratories, Inc., Elkhart, Ind.

[21] Appl. No.: 919,869

[22] Filed: Jun. 28, 1978

[51] Int. Cl.² ............... G01N 33/16; G01N 21/06; G01N 31/22
[52] U.S. Cl. ............... 23/230 B; 252/408; 422/56
[58] Field of Search ............... 23/230 B, 253 TP; 252/408

[56] References Cited

U.S. PATENT DOCUMENTS

| | | | |
|---|---|---|---|
| 2,290,436 | 7/1942 | Kamlet | 23/230 B |
| 2,799,660 | 7/1957 | Nicholls | 23/230 B X |
| 3,012,976 | 12/1961 | Adams | 23/230 B X |
| 3,092,463 | 6/1963 | Adams | 23/230 B X |
| 3,092,464 | 6/1963 | Adams | 23/230 B X |
| 3,853,472 | 12/1974 | Rittersdorf | 23/230 B |
| 3,917,452 | 11/1975 | Rittersdorf | 23/253 TP X |
| 3,975,161 | 8/1976 | Svoboda | 23/253 TP X |
| 3,986,833 | 10/1976 | Mast | 23/253 TP X |
| 4,066,408 | 1/1978 | Jonsson | 23/253 TP X |
| 4,071,317 | 1/1978 | Lam | 23/253 TP X |
| 4,071,318 | 1/1978 | Lam | 23/253 TP |
| 4,071,321 | 1/1978 | Lam | 23/253 TP |

*Primary Examiner*—Sidney Marantz
*Attorney, Agent, or Firm*—Roger N. Coe

[57] ABSTRACT

Improved test compositions, devices and methods are provided for detecting peroxidatively active substances in body fluids, body excreta and the like. The test compositions include an indicator or chromogen capable of being oxidized in the presence of a peroxidatively active substance to provide a color change, an oxidizing agent effective to oxidize said indicator or chromogen, and as a potentiating agent capable of enhancing the color obtained, a compound of the formula:

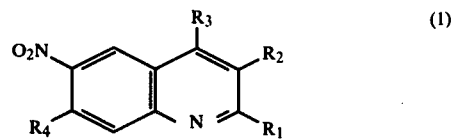

(I)

wherein $R_1$ is hydrogen, a lower alkyl group of 1 to 4 carbon atoms or hydroxy, and $R_2$, $R_3$ and $R_4$ are independently selected from hydrogen or a lower alkyl group of 1 to 4 carbon atoms; provided that at most only one R group is substituted.

8 Claims, No Drawings

TEST COMPOSITION, DEVICE AND METHOD FOR THE DETECTION OF PEROXIDATIVELY ACTIVE SUBSTANCES

FIELD OF THE INVENTION

The present invention relates to diagnostic compositions and devices for use in carrying out rapid analytical determinations and to methods for manufacturing and using such compositions and devices for the detection of peroxidatively active substances.

BACKGROUND OF THE INVENTION

The detection of small amounts of peroxidatively active substances such as occult blood, hemoglobin, myoglobin, etc., in body fluids and in body excreta has long been recognized as an invaluable aid to the medical practitioner in the diagnosis of many abnormal conditions. For example, blood found in urine, feces or vomit is important for the diagnosis of hemorrhages in the stomach, intestines and urinary tract. Such hemorrhages are caused, for example, by tumors, ulcers and inflammations of the corresponding organs. In urine, the presence of peroxidatively active substances may be indicative of such abnormal conditions as typhus, scurvy, purpura, pyemia, nephritis, third degree burns, carcinogenic conditions, disease and infection of the urinary system, hemolytic toxins and post cardiac infarct.

It has long been recognized that in the presence of a hydroperoxide a chromogen can be oxidized to a colored substance and thereby indicate the presence of a peroxidate-active substance. This reaction has been used for quite a long time in medicinal and forensic analysis, especially for the detection of blood. Typically hydrogen peroxide is employed as the hydroperoxide and as a chromogen there is preferably used benzidine, ortho-tolidine or leuko malachite green. Examples of various procedures, compositions and devices described in the literature for detection of occult peroxidatively active substances appear in U.S. Pat. Nos. 2,290,436; 2,799,660; 2,838,377; 3,012,976; 3,092,463 and 3,092,464, all assigned to the present assignee.

While the compositions mentioned in the referenced patents provide rapid means for the detection of occult blood, the compositions are relatively insensitive to especially minute quantities of peroxidatively active substances corresponding to blood dilutions of less than about 1:20,000, i.e., about 200 to 300 intact red blood cells per microliter of sample (RBC $\mu/l$). In U.S. Pat. No. 3,290,117 the sensitivity of occult blood test compositions was shown to be markedly improved by the addition of quinoline or certain quinoline derivatives such as quinine. With the addition of quinoline derivatives to prior art occult blood compositions it was demonstrated to be possible to detect 5 to 50 $\mu/l$ of sample corresponding to blood dilutions as low as 1:1,000,000. Similar sensitivities were obtained in U.S. Pat. No. 3,853,472 which discloses the use of fused polycyclic derivaties of quinoline as potentiating or activating agents. In addition, improved test compositions, devices and methods for detecting peroxidatively active substances are disclosed in U.S. Pat. No. 3,986,833. The latter patent makes specific reference to potentiating agents comprising acid salts or adducts of quinoline compounds.

Since the sensitivity of occult blood tests is of such great importance, it is essential that such tests not only be highly sensitive to peroxidatively active substances, but also retain their sensitivity. Unfortunately, except for the improved compositions containing quinine or certain other quinoline derivatives referred to in the prior art, many of the highly sensitive compositions which have been disclosed are unstable due to the volatility of added potentiators at room temperature or slightly above. Furthermore, virtually all of the prior art compositions utilize potentiators which are water insoluble and thus require suspension in organic solvents prior to incorporation into a test composition. It is common commercial practice for known potentiators to be suspended in an organic solvent solution containing the indicators. As a result, the indicators are often rapidly discolored in the presence of these potentiators and must be discarded. A desideratum of the art has been to provide test compositions which are not only rapid and highly sensitive, but which are also capable of retaining their sensitivity without discoloring the indicator system.

SUMMARY OF THE INVENTION

In accordance with the present invention, improved test compositions, devices and methods for the detection of peroxidatively active substances are provided which avoid the disadvantages of prior art compositions discussed above. Specifically, the test compositions include a chromogen or indicator capable of being oxidized in the presence of peroxidatively active substances to provide a color change, an oxidizing agent effective to oxidize the chromogen or indicator, and as a potentiating agent, a compound of the formula:

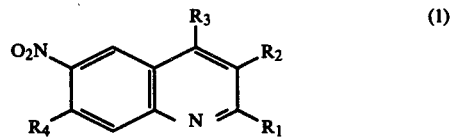

wherein $R_1$ is hydrogen, a lower alkyl group of 1 to 4 carbon atoms or hydroxy, and $R_2$, $R_3$ and $R_4$ are independently selected from hydrogen or a lower alkyl group of 1 to 4 carbon atoms; provided that at most only one R group is substituted.

DESCRIPTION OF THE PREFERRED EMBODIMENTS

Test compositions which can be improved by incorporation of the color enhancer or potentiating agent of the present invention contain at least an indicator and oxidizing agent and can be prepared in tablet form or incorporated with a carrier member or matrix such as an absorbent matrix.

Suitable indicators are those capable of being oxidized in the presence of peroxidatively active substances to provide a color change and include well known materials such as ortho-tolidine, ortho-toluidine, para-toluidine, ortho-phenylenediamine, N,N'-dimethyl-p-phenylenediamine, N,N'-diethyl-p-phenylenediamine, benzidine, p-anisidine, di-anisidine, o-cresol, m-cresol, p-cresol, α-naphthol, β-naphthol, catechol, guaiacol, pyrogallol or such indicators or chromogens as those of the heterocyclic azine series such as bis-(N-ethyl-quinol-2-one)-azine or (N-methylbenzthiazol-2-one)-(1-ethyl-3-phenyl-5-methtriazol-2-one)-azine.

As oxidizing agents materials such as cumene hydroperoxide, diisopropylbenzene hydroperoxide, paramethane hydroperoxide, 2,5-dimethylhexane-2,5-dihydroperoxide and other well known oxidizing agents effective to oxidize indicators or chromogens can be employed.

The color enhancer, as indicated above, is a compound selected from the class of compounds having the general formula:

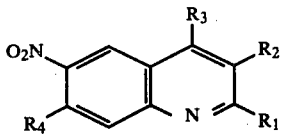

wherein $R_1$ is hydrogen, a lower alkyl group of 1 to 4 carbon atoms or hydroxy, and $R_2$, $R_3$ and $R_4$ are independently selected from hydrogen or a lower alkyl group of 1 to 4 carbon atoms; provided that at most only one R group is substituted. The compound 6-nitroquinone is particularly preferred. These compounds are either commercially available or are easily prepared from commercially available materials using synthesis techniques known to those skilled in the art.

In a preferred embodiment, improved test compositions of the present invention are incorporated on or with a matrix and utilized as a dip-and-read test device. Test devices can be prepared by various well known methods which include impregnating an absorbent matrix material with a solution or solutions of the test composition, printing or spraying a solution of the test composition on a matrix, etc. Normally the matrix with the solution therein and/ or thereon, is then dried and can be adhesively incorporated onto or affixed to a carrier member for ease of use. Suitable matrices which can be used include paper, cellulose, wood, synthetic resin fleeces, glass fiber, polypropylene felt, woven or nonwoven fabrics and the like. The preferable mode of preparation is to impregnate the matrix in two separate steps. For instance, the matrix is first impregnated with an aqueous mixture containing at least an oxidizing agent and compound of formula (1) and then drying the impregnated matrix material. The dried matrix is subsequently impregnated with a second mixture containing at least an indicator and an organic solvent and is again dried. The order of impregnation, however, is not critical. The dried impregnated matrix is thus prepared is advantageously affixed by suitable means, such as double-faced adhesive tape, to a carrier member, such as polystyrene, for ease of use.

In addition to the above test composition components which actively participate in the test reaction, further components such as thickening agents, wetting agents, buffers, emulsifying agents, and other well known adjuvants can also be included in the test composition or device of the present invention. Thus, for example, as thickening agents there can be used various materials such as gelatin, algin, carrageenin, casein, albumin, methyl cellulose, polyvinylpyrrolidone, and the like. As wetting agents, it is preferable to use sodium laurylsulfate, but any long chain organic sulfate or sulfonate, such as dioctyl sodium sulfosuccinate or sodium dodecylbensenesulfonate, can also be used. For buffering systems, tartarate, phosphate, phthalate, citrate, acetate, or succinate buffers can be used. Preferably, the compositions are buffered to a pH value from about 4 to about 7. As emulsifying agents, there can be used polyvinylalcohol, gum arabic, carboxyvinylpolymers and the like. Organic solvents which are useful to suspend indicators or chromogens include most nonreactive, volatile solvents such as chloroform, ethylenedichloride, benzene, ethyl acetate and the like.

In use, the matrix of the test device is momentarily immersed in or otherwise contacted by the liquid specimen or sample to be tested. In the presence of a peroxidatively active substance, the test composition gives a positive color reaction. The color which results is then compared with a predetermined color standard for an estimation of the quantitative amount of peroxidatively active substance contained in the specimen. Intact peroxidatively active substances, such as intact red blood cells, appear as dots or flecks of color on the otherwise uncolored matrix. Hemolyzed peroxidatively active substances uniformly color the matrix and may be easily distinguished from the intact peroxidatively active substances. In addition to visual comparison, various instrumental methods can also be employed to determine the quantity of color developed, thus increasing the accuracy of the test by obviating the subjective determination of color by the human eye.

It has been found that the improved test compositions and device of the present invention are not only stable, but are highly sensitive. The instant test compositions are capable of detecting even individual intact peroxidatively active substances at concentrations as low as 5 to 20 RBC/$\mu$l of sample which corresponds to a blood dilution as low as 1:1,000,000. This high degree of sensitivity for test compositions incorporating compounds of the general formula (1) is indeed unexpected and advantageous.

The following illustrative examples are provided to further describe the invention, but are not intended to limit the scope of the invention.

EXAMPLE I

Filter paper is successively impregnated with the following solutions and dried at 60° C. after each impregnation:

| First Impregnation Solution | |
|---|---|
| 2,5-dimethylhexyl-2,5-dihydroxy peroxide | 3 grams (g) |
| ethylenediaminetetraacetic acid (EDTA) | 0.2 g |
| sodium lauryl sulfate | 2.0 g |
| 1.2 M citrate buffer, pH 5.6 | 35 milliliters (ml) |
| 2% Natrosol KR 250 (hydroxyethylcellulose) | 100 ml |
| ethanol | 30 ml |
| water | 35 ml |

After drying the impregnated filter paper at 60° C. for 60 minutes, it is further impregnated with the following solution:

| Second Impregnation Solution | |
|---|---|
| o-tolidine | 0.3 g |
| 6-nitroquinoline | 0.4 g |
| chloroform | 100 ml |

The resulting impregnated filter paper is dried at 60° C. for 30 minutes. A pale yellow test paper is obtained. When the test paper is dipped into a urine sample containing intact or hemolyzed erythrocytes, a green color is developed after 5 to 20 seconds. When the test paper is dipped into a urine specimen containing intact red blood cells green dots appear on the test paper, and when free hemoglobin is present in the urine specimen tested, a uniform green color is developed on the test paper. The sensitivity is approximately 5 to 20 intact RBC/μl or a hemoglobin equivalent of 10 to 40 hemolyzed RBC/μl.

EXAMPLE II

Filter paper is successively impregnated with the following solutions and dried at 60° C. after each impregnation:

| First Impregnation Solution | |
|---|---|
| 2,5-dimethylhexyl-2,5-dihydroxy peroxide | 3 grams (g) |
| ethylenediaminetetraacetic acid (EDTA) | 0.2 g |
| sodium lauryl sulfate | 2.0 g |
| 1.2 M citrate buffer, pH 5.6 | 35 milliliters (ml) |
| 2% Natrosol KR 250 (hydroxyethylcellulose) | 100 ml |
| ethanol | 30 ml |
| water | 35 ml |

After drying the impregnated filter paper at 60° C. for 60 minutes, it is further impregnated with the following solutions:

| Second Impregnating Solution | |
|---|---|
| o-tolidine | 0.3 g |
| 1-ethyl-6-nitroquinoline | 0.4 g |
| chloroform | 100 ml |

The resulting impregnated filter paper is dried at 60° C. for 30 minutes. Portions of the resulting test paper are dipped into urine samples containing intact or hemolyzed erythrocytes and observed for color development. When the sample tested contain intact red blood cells green dots appear on the test paper, and when free hemoglobin is present in the specimen, a uniform green color is developed on the test paper.

EXAMPLE III

Filter paper is successively impregnated with the following solutions and dried at 60° C. after each impregnation:

| First Impregnation Solution | |
|---|---|
| 2,5-dimethylhexyl-2,5-dihydroxy peroxide | 3 grams (g) |
| ethylenediaminetetraacetic acid (EDTA) | 0.2 g |
| sodium lauryl sulfate | 2.0 g |
| 1.2 M citrate buffer, pH 5.6 | 35 milliliters (ml) |
| 2% Natrosol KR 250 (hydroxyethylcellulose) | 100 ml |
| ethanol | 30 ml |
| water | 35 ml |

After drying the impregnated filter paper at 60° C. for 60 minutes, it is further impregnated with the following solution:

| Second Impregnating Solution | |
|---|---|
| o-tolidine | 0.3 g |
| 3-methyl-6-nitroquinoline | 0.4 g |
| chloroform | 100 ml |

The resulting impregnated filter paper is dried at 60° C. for 30 minutes. Portions of the resulting test paper are dipped into urine samples containing intact or hemolyzed erythrocytes and observed for color development. When the sample tested contain intact red blood cells, green dots appear on the test paper, and when free hemoglobin is present in the sample tested, a uniform green color is developed on the test paper.

Similar results can also be obtained when the procedure of Example III is followed except for the substitution of 1-hydroxy-6-nitroquinoline for 3-methyl-6-nitroquinoline.

From the foregoing, it will be seen that this invention is well adapted to attain all of the ends and objects hereinabove set forth together with other advantages which are obvious and which are inherent to the system. The compounds of formula (1) have greater color enhancing properties for hemoglobin detection system than the quinine alkaloid compounds described in the prior art. It is, of course, obvious that not all of the compounds coming within the scope of general formula (1) possess activating properties of the same degree. Thus, it is possible to adjust the sensitivity of, for example, a blood test in accordance with practical requirements.

The compositions of the present invention can be used for analytical determinations of, for example, glucose, galactose, aminoacids, uric acid, peroxide, hemoglobin, peroxidase, etc., in samples constituting biological fluids such as blood, urine, spinal fluid, etc.; milk; and cosmetic and drug formulations, etc.

Obviously, many other modifications and variations of the invention as hereinabove set forth may be made without departing from the spirit and scope thereof.

What is claimed is:

1. A test composition for detection of peroxidatively active substances in body fluids, body excreta, and the like, of the type including an indicator capable of being oxidized in the presence of a peroxidatively active substance to provide color change, an oxidizing agent effective to oxidize said indicator, and a potentiating agent, wherein said potentiating agent comprises a compound having the formula:

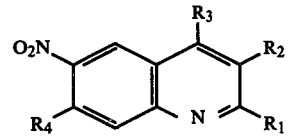

wherein $R_1$ is hydrogen, a lower alkyl group of 1 to 4 carbon atoms or hydroxy, and $R_2$, $R_3$ and $R_4$ are independently selected from hydrogen or a lower alkyl group of 1 to 4 carbon atoms; provided that at most only one R group is substituted.

2. A composition according to claim 1 in which the potentiating agent is 6-nitroquinoline.

3. A composition according to claim 1 in which the potentiating agent is 1-ethyl-6-nitroquinoline.

4. A composition according to claim 1 in which the potentiating agent is 3-methyl-6-nitroquinoline.

5. A test device for detecting peroxidatively active substances in body fluids, body excreta, and the like, of the type having a carrier matrix incorporated with an oxidizing agent, an indicator and a potentiating agent, wherein said potentiating agent comprises a compound of the general formula:

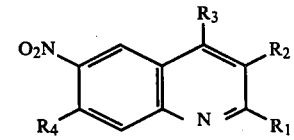

wherein $R_1$ is hydrogen, a lower alkyl group of 1 to 4 carbon atoms or hydroxy, and $R_2$, $R_3$ and $R_4$ are independently selected from hydrogen or a lower alkyl group of 1 to 4 carbon atoms; provided that at most only one R group is substituted.

6. The test device of claim 5 in which the carrier matrix is a bibulous cellulose paper matrix.

7. A method for detecting minor amounts of peroxidatively active substance in body fluids, body excreta, and the like, which method comprises contacting a test sample of the body fluids or excreta with the carrier matrix of a test device as claimed in claim 5 and observing a color formation thereon as an indication of the presence of a peroxidatively active substance in said sample.

8. A method according to claim 7 wherein the peroxidatively active substance is occult blood.

* * * * *